United States Patent [19]

Beebe

[11] Patent Number: 5,545,038
[45] Date of Patent: Aug. 13, 1996

[54] PERCUSSIVE DENTAL EXTRACTOR

[75] Inventor: Deborah V. Beebe, Jupiter, Fla.

[73] Assignee: Sidney Horowitz, Jupiter, Fla.

[21] Appl. No.: 508,205

[22] Filed: Jul. 27, 1995

[51] Int. Cl.$^6$ ............................... A61C 1/07; A61C 3/08
[52] U.S. Cl. .............................. 433/120; 433/121
[58] Field of Search ................... 433/150, 151, 433/121, 164, 120

[56] References Cited

U.S. PATENT DOCUMENTS

| | | | |
|---|---|---|---|
| 158,863 | 1/1875 | Nichols | 433/120 |
| 487,843 | 12/1892 | Kline | 433/151 |
| 492,830 | 3/1893 | Peck | 433/120 |
| 513,362 | 1/1894 | Foster et al. | 433/120 |
| 577,887 | 3/1897 | Stanton | 433/151 |
| 4,300,885 | 11/1981 | Khait | 433/151 |
| 5,496,172 | 3/1996 | Albelda et al. | 433/120 |

*Primary Examiner*—Cary E. O'Connor
*Attorney, Agent, or Firm*—Larson and Taylor

[57] ABSTRACT

A pneumatically operated percussive dental extractor includes a main body having a central longitudinal chamber. A replaceable hook member is attached to the distal end of the main body. Mounted in the longitudinal chamber at a proximal end thereof is an anvil. Reciprocally mounted in the longitudinal chamber for movement from a distal end thereof to engagement with the anvil is a piston. A driving device selectively drives the piston pneumatically from the distal end of the chamber into percussive engagement with the anvil. A return device automatically returns the piston from engagement with the anvil to the distal end of the chamber. The driving device includes a coupling located at the proximal end of the main body for connecting the driving device to a source of pneumatic pressure and a trigger device for selectively connecting the source of pneumatic pressure to the distal end of the chamber. The trigger device includes an actuator which is radially moved to connect the pneumatic source to the distal end of the chamber. The driving device further includes a control device for controlling the pneumatic pressure exerted on the piston and a hollow shaft which extends from the proximal end to the distal end of the chamber with an air outlet at a distal end thereof into the distal end of the chamber. The piston is then mounted for movement about the hollow shaft, and the return device includes a compression spring located about the hollow shaft between the piston and the anvil.

7 Claims, 2 Drawing Sheets

{ 5,545,038 }

PERCUSSIVE DENTAL EXTRACTOR

FIELD OF THE INVENTION

The present invention relates generally to a device for the separation of a crown or caps from a tooth, and more particularly to a percussive dental extractor which is pneumatically operated.

BACKGROUND OF THE INVENTION

In dentistry, it is necessary to remove temporary caps or crowns (hereafter crowns) and sometimes to remove permanent crowns from a shaped tooth. Various means have been employed to force the crown from the tooth. One such device is disclosed in U.S. Pat. No. 4,300,885 (Khait). The disclosed device is a spring-loaded percussive mechanism which has a hooked end to supply a removing jolt to the crown.

While the prior art devices or methods have been acceptable, a more readily usable and easily operated device is desirable.

SUMMARY OF THE INVENTION

In accordance with the present invention, a pneumatically operated percussive dental extractor comprises a main body having a longitudinal axis, a central longitudinal chamber, a proximal end and a distal end. A replaceable hook member is attached to the distal end of the main body. Mounted in the longitudinal chamber at a proximal end thereof is an anvil. Reciprocally mounted in the longitudinal chamber for movement from a distal end thereof to engagement with the anvil is a piston. A driving means is then provided for selectively driving the piston pneumatically from the distal end of the chamber into percussive engagement with the anvil. After percussive engagement with the anvil, a return means automatically returns the piston from engagement with the anvil to the distal end of the chamber.

In a preferred embodiment, the driving means includes a coupling located at the proximal end of the main body for connecting the driving means to a source of pneumatic pressure and a trigger means for selectively connecting the source of pneumatic pressure to the distal end of the chamber. The trigger means preferably includes an actuator which is radially moved to connect the pneumatic source to the distal end of the chamber. The driving means further includes a control means for controlling the pneumatic pressure exerted on the piston.

In the preferred embodiment, the main body includes a handle, a barrel, and an attaching means for removably attaching the barrel to the handle at the proximal end of the handle. With this configuration, the barrel includes the coupling, the trigger means and the control means. The driving means also includes a hollow shaft which extends from the proximal end to the distal end of the chamber and which has an air outlet at a distal end thereof into the distal end of the chamber. The piston is then mounted for movement about the hollow shaft, and the return means includes a compression spring located about the hollow shaft between the piston and the anvil.

For improved sanitation, the hook member is made of a plastic material and is disposable after use. An attaching means is then provided for removably attaching the hook member to the distal end of the handle.

It is an advantage of the present invention that a dental extractor is provided which is easy and simple to operate.

It is also an advantage of the present invention that a dental extractor is provided which is reliably and conveniently powered by a pneumatic gas source.

It is a further advantage of the present invention that a dental extractor is provided which has a percussive force which is variable as desired.

It is still a further advantage that a disposable hook member is provided.

Other features and advantages of the present invention are stated in or apparent from a detailed description of a presently preferred embodiment of the invention found hereinbelow.

DETAILED DESCRIPTION OF THE PREFERRED EMBODIMENT

Figure 1:
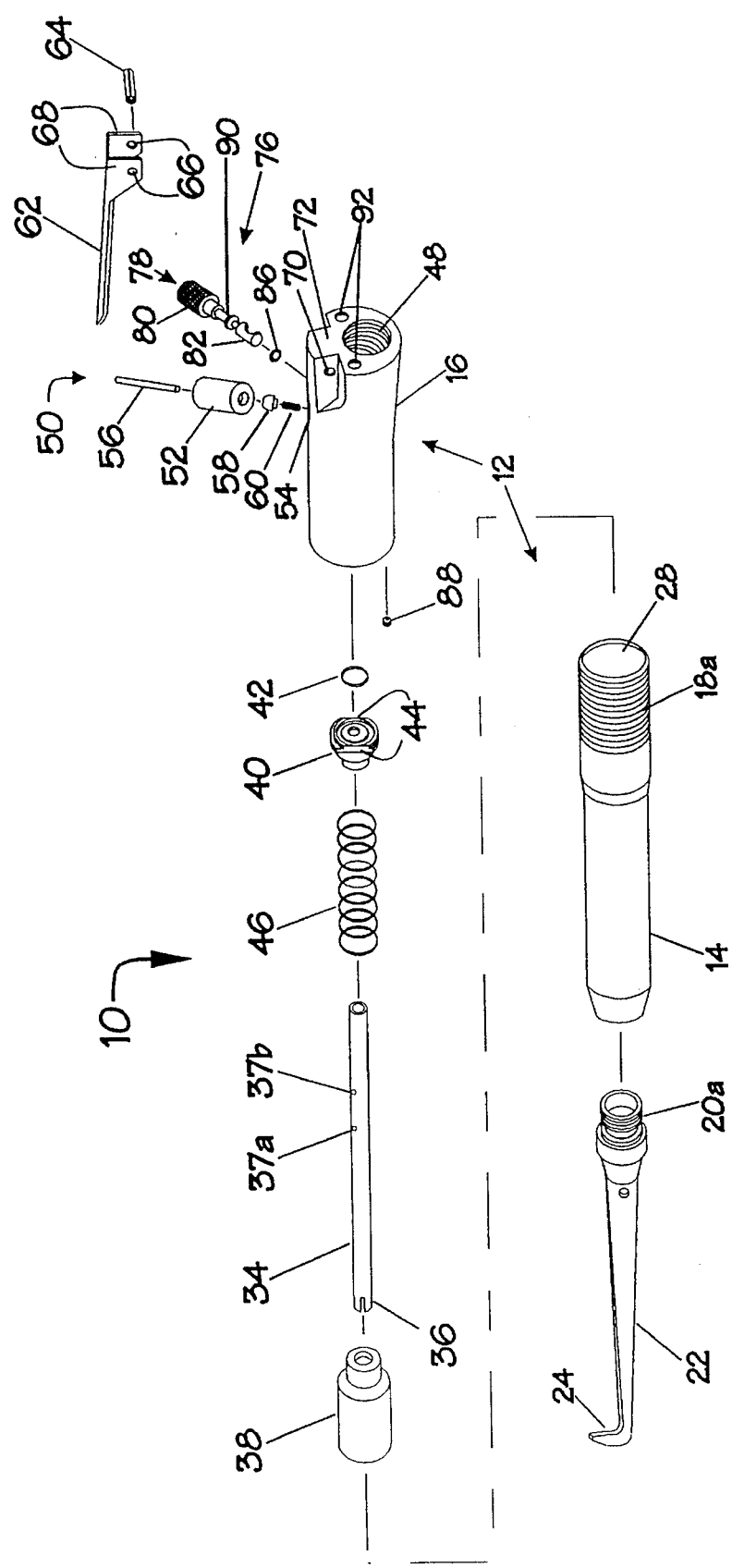
FIG. 1 is an exploded perspective view of the percussive dental extractor of the present invention.
Figure 2:
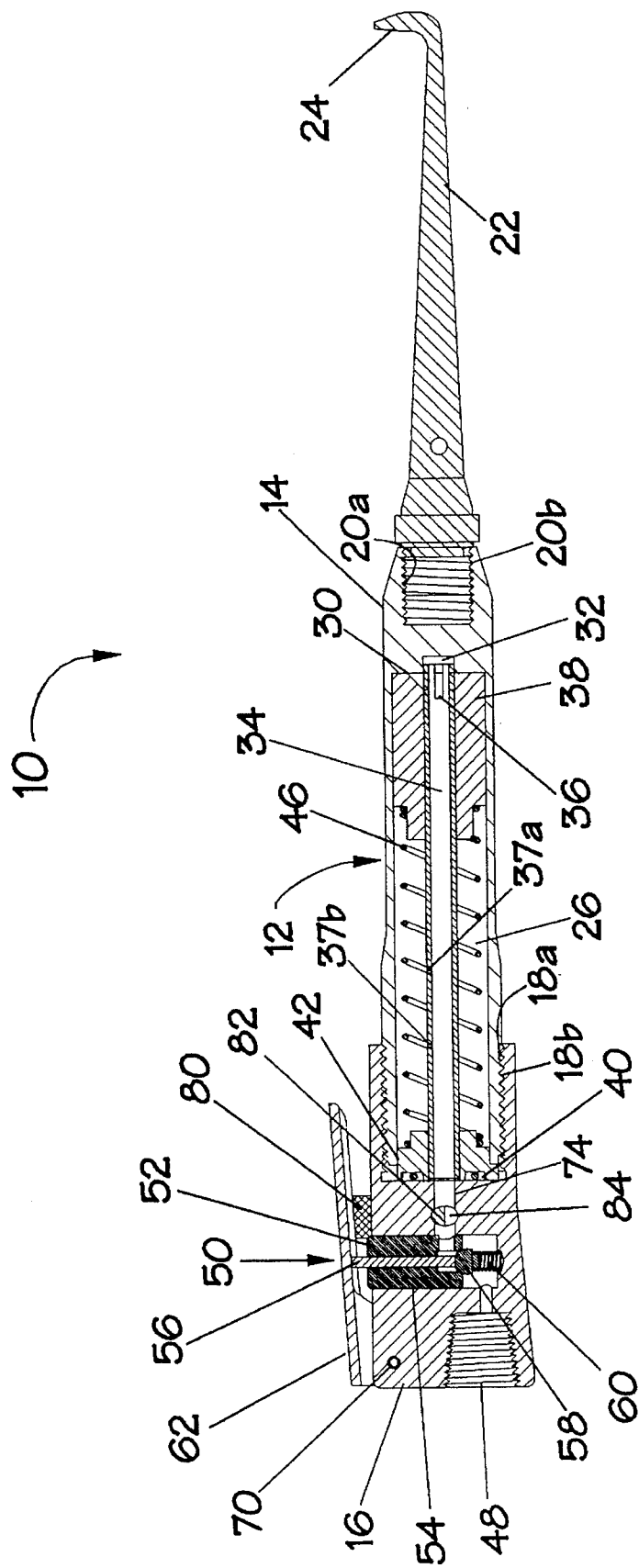
FIG. 2 is a longitudinal cross-sectional elevation view of the dental extractor depicted in FIG. 1.

With reference now to the drawings in which like numerals represent like elements throughout the two views, a preferred percussive dental extractor 10 according to the present invention is depicted in FIGS. 1 and 2. Dental extractor 10 includes a main body 12 comprised of a handle 14 at a distal end thereof and a barrel 16 at a proximal end thereof. Handle 14 and barrel 16 are attached together by mating threads 18*a* and 18*b*. Attached by suitable mating screw threads 20*a* and 20*b* at the distal end of handle 14 is a hook member 22. Hook member 22 includes a hook 24 at the distal end thereof which is placed under the crown when removal is desired using dental extractor 10. Preferably, hook member 22 made of a hard plastic and is disposable after use.

As shown, handle 14 is hollow and defines a cylindrical chamber 26, having an opening 28 and a bottom 30. Provided in bottom 30 is a locating hole 32. Mounted in locating hole 32 is a distal end of a hollow shaft 34. At this distal end, hollow shaft 34 includes short slots 36. Intermediate the length of hollow shaft 34 are small vent holes 37*a* and 37*b*. A piston 38 is then mounted for longitudinal movement in chamber 26 from bottom 30 to opening 28. Located at opening 28 and about hollow shaft 34 is an anvil 40. Anvil 40 is trapped between the proximal end of handle 14 and the distal end of barrel 16 as threads 18*a* and 18*b* are mated. An O-ring 42 is located between anvil 40 and the adjacent surface of barrel 16 to form an air-tight fit between anvil 40 and barrel 16. It will be appreciated that anvil 40 includes flat sides 44, and thus is not completely cylindrical and does not completely fill opening 28. Disposed between anvil 40 and piston 38 is a compression spring 46 which urges piston 38 away from anvil 40.

Barrel 16 includes a coupling 48 by which dental extractor 10 is connected to a suitable source of pneumatic pressure. Preferably, a quick disconnect member (not shown) is threadably engaged in coupling 48 so that dental extractor 10 is easily and quickly connected and disconnected from the pneumatic pressure source. Associated with barrel 16 is a trigger means 50 which controls the application of pneumatic pressure to piston 38. Trigger means 50 includes a valve body 52 located in a suitable hole 54 in barrel 16. Extending slidably through valve body 52 is an actuator or valve stem 56. At one end, valve stem 56 engages a mushroom cap 58 which is urged into contact with valve body 52 by a spring 60. At the other end, valve stem 56 engages a lever 62 which is pivotally mounted to barrel 16 by a pin 64. As shown, pin 64 passes through holes 66 provided in ears 68 of lever 62 and engages in hole 70 provided in recessed portion 72 of barrel 16 so that lever is held in place on barrel 16.

Extending longitudinally from the outlet of valve body 52 is a passage 74 in barrel 16. As shown, passage 74 aligns with hollow shaft 34. Provided in passage 74 is a control means 76 for controlling or varying the pressure of the pneumatic source passing thereby. Control means 76 includes a regulator 78 having a knurled knob 80 at one end and a laterally concave tip 82 at the other end. Control means 76 is inserted in a hole 84 drilled at a 45° angle (about the longitudinal axis of barrel 16) to hole 54 in barrel 16. An O-ring 86 surrounds regulator 78 outwardly from tip 82 to prevent pressurized air from escaping along regulator 78. A set screw 88 is inserted longitudinally in barrel 16 to engage a land 90 of regulator 78 to hold regulator 78 rotatably in place in barrel 16 with knob 80 extending from barrel 16 and with tip 82 located in passage 74. Barrel 16 also includes two passages 92 longitudinally therethrough which have distal ends located in chamber 26 adjacent (but not covered by) flat sides 44 of anvil 40.

In operation, dental extractor 10 functions in the following manner. Initially, it will be appreciated that dental extractor 10 is connected via coupling 48 to a suitable source (not shown) of pressurized gas, such as a compressor typically found in a dentist's office. When it is desired to remove a crown from a patient's mouth, dental extractor 10 is positioned so that hook 24 of hook member 22 is located between the crown and the tooth. The dentist then presses on lever 62. The short pivotal movement of lever 62 about pin 64 causes valve stem 56 to move radially inward, pushing mushroom cap 58 away from valve body 52. This movement of mushroom cap 58 thus allows the pressurized air from the source to flow through valve body 52, past tip 82 of control means 76 and through hollow shaft 34. At the distal end of hollow shaft 34, the pressurized air exits through slots 36 and fills the space between piston 38 and bottom 30. This pressurized air thus causes piston 38 to be thrust away from bottom 30 until piston 38 slams into anvil 40. The force of impact on anvil 40 (or rather the momentum of piston 38) is then immediately transferred to the remainder of dental extractor 10 including hook 24, causing the crown to be jolted quickly from the tooth as hook 24 (and the remainder of dental extractor 10) is jolted backwards away from the tooth. During the movement of piston 34 into anvil 40, it will be appreciated that the ambient air within chamber 26 is exhausted through passages 92.

Once piston 34 slams into anvil 40, lever 62 is released by the dentist. Until lever 62 is released, it will be appreciated that the holding of lever 62 in the depressed position does not affect dental extractor 10 as the air pressure filling chamber 26 merely holds piston 38 in place against anvil 40 and against the pressure of spring 46. Once lever 62 is released, mushroom cap 58 returns to the position of engagement with valve body 52 and thus cuts off the source of pressurized gas from hollow shaft 34. With the source of pressurized gas cut off, spring 46 begins to move piston 38 back towards bottom 30. As this occurs, the gas located between piston 38 and bottom 30 is vented through vent holes 37a and 37b into chamber 26 and finally out of passages 92 to ambient atmosphere.

If the crown is not extracted from the tooth after an operation of dental extractor 10, shortly after release of lever 62, dental extractor will return to the beginning position and be ready to be actuated again after hook 24 is again properly positioned (or the position thereof checked).

While the present invention has been described with respect to an exemplary embodiment thereof, it will be understood by those of ordinary skill in the art that variations and modifications can be effected within the scope and spirit of the invention.

What is claimed is:

1. A pneumatically operated percussive dental extractor comprising:

a main body having a longitudinal axis, a central longitudinal chamber, a proximal end and a distal end;

a hook member attached to the distal end of said main body;

an anvil mounted in said longitudinal chamber at a proximal end thereof;

a piston reciprocally mounted in said longitudinal chamber for movement from a distal end thereof to engagement with said anvil;

a driving means for selectively driving said piston pneumatically from the distal end of said chamber into percussive engagement with said anvil, said driving means including a coupling for connecting the driving means to a source of pneumatic pressure located at the proximal end of said main body and a trigger means for selectively connecting the source of pneumatic pressure to the distal end of said chamber, said trigger means including an actuator which is radially moved to connect the pneumatic source to the distal end of said chamber; and a return means for automatically returning said piston from engagement with said anvil to the distal end of said chamber.

2. A percussive dental extractor as claimed in claim 1 wherein said driving means further includes a control means for controlling the pneumatic pressure exerted on said piston.

3. A percussive dental extractor as claimed in claim 2 wherein said main body includes a handle, a barrel, and an attaching means for removably attaching said barrel to said handle at the proximal end of said handle, said barrel including said coupling, said trigger means and said control means.

4. A percussive dental extractor as claimed in claim 3 wherein said driving means includes a hollow shaft which extends from said proximal end to said distal end of said chamber and which has an air outlet at a distal end thereof into the distal end of said chamber, wherein said piston is mounted for movement about said hollow shaft, and wherein said return means includes a compression spring located about said hollow shaft between said piston and said anvil.

5. A percussive dental extractor as claimed in claim 4 wherein said hook member is made of a plastic material, and further including an attaching means for removably attaching said hook member to the distal end of said handle.

6. A percussive dental extractor as claimed in claim 1 wherein said driving means includes a hollow shaft which extends from said proximal end to said distal end of said chamber and which has an air outlet at a distal end thereof into the distal end of said chamber, wherein said piston is mounted for movement about said hollow shaft, and wherein said return means includes a compression spring located about said hollow shaft between said piston and said anvil.

7. A percussive dental extractor as claimed in claim 1 wherein said hook member is made of a plastic material, and further including an attaching means for removably attaching said hook member to the distal end of said main body.

* * * * *